United States Patent
Schultz

(10) Patent No.: US 6,506,804 B2
(45) Date of Patent: Jan. 14, 2003

(54) ETHYLENICALLY UNSATURATED AMINE SALTS OF SULFONIC, PHOSPHORIC, AND CARBOXYLIC ACIDS

(75) Inventor: Alfred K. Schultz, Lake Villa, IL (US)

(73) Assignee: Stepan Company, Northfield, IL (US)

( * ) Notice: Subject to any disclaimer, the term of this patent is extended or adjusted under 35 U.S.C. 154(b) by 0 days.

(21) Appl. No.: 09/801,943

(22) Filed: Mar. 8, 2001

(65) Prior Publication Data

US 2001/0018461 A1 Aug. 30, 2001

Related U.S. Application Data

(63) Continuation of application No. 09/060,238, filed on Apr. 14, 1998, now abandoned, which is a continuation of application No. 08/790,360, filed on Jan. 28, 1997, now abandoned.

(51) Int. Cl.$^7$ ................................................. B01F 17/00
(52) U.S. Cl. .................... 516/59; 510/127; 524/814; 524/817; 525/919; 526/287; 562/84; 562/114; 516/63; 516/64; 516/910; 516/914
(58) Field of Search ............................. 516/59, 63, 64; 510/299, 27; 524/814, 817; 526/911, 923, 287; 525/919; 562/84, 114

(56) References Cited

U.S. PATENT DOCUMENTS

| | | | |
|---|---|---|---|
| 2,941,969 A | 6/1960 | Price | 524/197 |
| 3,129,195 A | 4/1964 | June et al. | 524/817 |
| 3,308,081 A | 3/1967 | Glabisch | 524/813 |
| 3,539,522 A | 11/1970 | Lindner | 516/59 X |
| 3,759,982 A | 9/1973 | Samour | 560/196 |
| 3,925,442 A | 12/1975 | Samour | 558/28 |
| 3,957,699 A | * 5/1976 | Solomon et al. | 526/923 X |
| 4,049,608 A | 9/1977 | Steckler et al. | 524/817 |
| 4,377,185 A | 3/1983 | Wessling et al. | 138/90 |
| 4,617,343 A | 10/1986 | Walker | 524/817 |
| 4,626,577 A | * 12/1986 | Harada | 526/287 X |
| 4,968,451 A | 11/1990 | Scheibel et al. | 510/299 |
| 5,162,475 A | 11/1992 | Tang et al. | 526/333 |
| 5,250,642 A | 10/1993 | Ahmed et al. | 526/240 |
| 5,478,883 A | 12/1995 | Anchor et al. | 524/812 |
| 5,563,214 A | 10/1996 | Share et al. | 524/809 |
| 5,567,356 A | 10/1996 | Kinlen | 252/500 |
| 5,863,465 A | 1/1999 | Kinlen | 252/500 |
| 5,928,783 A | * 7/1999 | Phan et al. | 526/287 X |
| 5,962,580 A | * 10/1999 | Nkansah et al. | 526/287 X |
| 5,969,032 A | * 10/1999 | Phan et al. | 524/460 |
| 6,239,240 B1 | * 5/2001 | Schultz et al. | 526/287 X |

FOREIGN PATENT DOCUMENTS

| | | |
|---|---|---|
| DE | 3426197 A1 | 1/1996 |
| SU | 223330 | 8/1968 |

* cited by examiner

Primary Examiner—Richard D. Lovering
(74) Attorney, Agent, or Firm—McDonnell Boehnen Hulbert & Berghoff

(57) ABSTRACT

Disclosed are ethylenically unsaturated amine salts of sulfonic, phosphoric and carboxylic acids. The salts are surface active agents which are useful in a variety of applications as primary and/or secondary surfactants. The salts are especially useful as surfactants in emulsion polymerization reactions.

10 Claims, No Drawings

US 6,506,804 B2

ETHYLENICALLY UNSATURATED AMINE SALTS OF SULFONIC, PHOSPHORIC, AND CARBOXYLIC ACIDS

This is a continuation of application Ser. No. 09/060,238, filed Apr. 14, 1998, now abandoned, which is a continuation of application Ser. No. 08/790,360, filed Jan. 28, 1997, now abandoned.

BACKGROUND OF THE INVENTION

1. Field of the Invention

The present invention relates to novel ethylenically unsaturated amine salts of sulfonic, phosphoric and carboxylic acids. More specifically, the invention relates to ethylenically unsaturated amine salts of alkylbenzene sulfonic acids, alkyl olefin sulfonic acids, alkyl alcohol sulfuric acid esters and alkoxylated alkyl alcohol sulfuric acid esters, and mixtures thereof. Additionally, the invention relates to ethylenically unsaturated amine salts of alkyl carboxylic acids and alkyl phosphoric acids. The salts are polymerizable, surface active agents which are useful in a variety of applications, especially in detergent formulations and in emulsion polymerization processes.

2. Description of the Related Art

Detergents, shampoos, cleansers, soaps, and the like, are used to perform a wide variety of household and industrial cleaning operations and are formulated to give compositions which produce optimum performance under the contemplated end use conditions. Typically, these compositions contain a variety of surface active agents known to the art, in the form of anionic, nonionic, amphoteric, and/or cationic surfactants. The anionic surfactants used in the compositions are typically in the form of alkali metal (lithium, sodium, potassium), alkaline earth (calcium, magnesium), ammonium and/or alkanolamine salts of the corresponding anionic acid. In formulating such compositions, it is desirable to have a variety of surface active agents available for producing and optimizing the compositions.

Surface active agents also find use in applications beyond typical detergent or shampoo formulations. For example, in a conventional emulsion polymerization of ethylenically unsaturated monomers, one or more surfactants are used to emulsify the monomers and the resulting polymer products, i.e., latexes. The monomers used in emulsion polymerization reactions are generally water-insoluble, but may also be water-soluble. During the polymerization, small portions of monomer are suspended in a continuous aqueous phase. Typically, a water soluble surfactant is present within the aqueous phase to aid in the suspension of the monomer, with subsequent polymerization via a free-radical polymerization. The water soluble surface active agents, i.e., surfactants, utilized in emulsion polymerization reactions are typically anionic, nonionic, cationic, or zwitterionic surfactants or mixtures thereof.

In a traditional emulsion polymerization reaction, discrete, solid polymeric particles are formed during the course of the reaction to form a polymer product latex. Typically, the surfactant employed in such a traditional emulsion polymerization reaction does not react with, i.e., become chemically bonded via carbon-carbon bond formation, the discrete polymeric particles. Rather, the surfactant remains unreacted in the polymer product latex after the emulsion polymerization reaction is complete. The unreacted surfactant can interfere with the performance of such polymerization products in coating, adhesive, sealant and elastomer (CASE) applications, non-woven fiber applications and carpet backings. The unreacted surfactant may cause pealing of a latex paint coating, and decreased moisture resistance and scrubability resistance in various CASE applications. Additionally, residual surfactant can cause an undesirable "blooming" that leads to surface irregularities in a resulting CASE that is applied to a substrate.

Several proposals have been made in the prior art to employ a polymerizable surfactant as the surface active agent during an emulsion polymerization reaction. U.S. Pat. No. 5,478,883 (incorporated herein by reference) describes the use of ethylenically unsaturated polymerizable water-soluble nonionic surfactants formed by the reaction of a diallylamine compound with ethylene oxide, propylene oxide or butylene oxide, in emulsion polymerization reactions. Similarly, U.S. Pat. No. 5,162,475 (incorporated herein by reference) provides alpha-beta ethylenically unsaturated poly(alkylenoxy) polymerizable surface active compounds for use in emulsion polymerization. For additional examples of polymerizable surfactants for use in emulsion polymerization processes, see U.S. Pat. Nos. 4,377,185 and 4,049,608.

SUMMARY OF THE INVENTION

The present invention provides ethylenically unsaturated amine salts of sulfonic, phosphoric or carboxylic acids, or mixtures thereof. The amine salts of the present invention are polymerizable, surface active agents suitable for use as primary or secondary surfactants, and/or as surfactants in emulsion polymerization reactions.

Accordingly, the present invention provides novel ethylenically unsaturated amine salts of sulfonic, phosphoric or carboxylic acids, or mixtures thereof, which are polymerizable, surface active agents in a variety of applications. It has been discovered that these surface active agents are useful, for example, in detergents (e.g., laundry detergents, dish detergents, automatic dishwasher detergents, etc.), shampoos, 2-in-1 shampoos, 3-in-1 shampoos, cleansers, soaps, liquid hand soaps, body washes, agricultural herbicide and pesticide formulations and the like. Additionally, the surface active agents of the present invention are especially useful in emulsion polymerization reactions and are generally capable of polymerizing with themselves and/or co-polymerizing with other ethylenically unsaturated monomers of the type which are commonly employed in emulsion polymerization reactions.

The surface active agents of the present invention are prepared from readily available, economical raw materials, and generally, their preparation does not require any special handling or equipment. The polymerizable surface active agents may be prepared in a batch mode or a continuous mode; they may be prepared by contacting the ethylenically unsaturated amine with the acid or contacting the acid with the ethylenically unsaturated amine. By contacting it is meant that the acid(s) is added to the ethylenically unsaturated amine(s) and the components are mixed, or the ethylenically unsaturated amine(s) is added to the acid(s) and the components are mixed. Typically, the acid is present as an anion and the base is present as a cation (i.e. a quaternary nitrogen) in the mixture. The acid and nitrogenous base form salts or quaternary nitrogen compounds. As known by one skilled in the art, upon mixing the acid and nitrogenous base together, the nitrogenous base becomes a conjugate acid and the acid becomes a conjugate base.

The surface active agents and blends of surface active agents may be prepared in a variety of forms, including but not limited to, liquids, solutions, solids, powders, flakes, semi-solids, gels, "ringing" gels, G-phase liquids, hexagonal phase solids, or thick pastes. The surface active agents may be spray dried, flaked, extruded, and the like. Although not critical to the present invention, the polymerizable, surface active agents may be prepared "neat" or in a conventional solvent such as water, low molecular weight alcohol or hydrocarbon, or a mixture thereof, to produce an aqueous solution of the surface active agent The present invention encompasses surface active agents as salts in dry form and as aqueous solutions. Salts of the surface active agents may be isolated by drying a solution of the surface active agents; a solution of surface active agents may be prepared by dissolving the salt of the surface active agent in water, low molecular weight alcohol or hydrocarbon, or a mixture thereof.

Individual surface active agents of the present invention may be prepared and mixed together to produce a surface active mixture comprising "neat" surface active agents or an aqueous surfactant blend. Additionally, neat or aqueous blends of the surface active agents may be prepared by contacting a blend of two or more ethylenically unsaturated amines with one acid, or by contacting a blend of two or more ethylenically unsaturated amines with a blend of 2 or more acids. Conversely, blends of the surface active agents may be prepared by contacting a blend of two or more acids with one ethylenically unsaturated amine, or by contacting a blend of two or more acids with a blend of two or more ethylenically unsaturated amines.

These and other advantages of the present invention will be apparent from the following description of the invention.

DETAILED DESCRIPTION OF THE INVENTION

The present invention encompasses polymerizable, surface active agents which are salts or quaternary nitrogen compounds comprising:

a) at least one acid, wherein the acid is a sulfonic acid, a carboxylic acid, or a phosphoric acid, or mixtures thereof; and b) at least one nitrogenous base, wherein the nitrogenous base contains at least one nitrogen atom and at least one ethylenically unsaturated moiety.

The polymerizable surface active agents of the present invention are salts or quaternary nitrogen compounds comprising at least one acid, wherein the acid is a sulfonic acid, a carboxylic acid, or a phosphoric acid, or a mixture thereof, and at least one nitrogenous base, wherein the nitrogenous base contains at least one nitrogen atom and at least on ethylenically unsaturated moiety. In general, although not required, the polymerizable surface active agents have a homophilic/lipophilic balance (HLB) of less than about 45. In a somewhat more preferred embodiment, the polymerizable surface active agents have an HLB of about 5–40. The polymerizable surface active agents are generally capable of polymerization with themselves, co-polymerization with the ethylenically unsaturated monomer, or co-polymerization with a partially polymerized polymer.

More specifically, while the nitrogenous base may be capable of some degree of surface activity, in the present invention it is the acid portion of the polymerizable surfactant that is responsible for the surfactant character of the compound. In preferred embodiments, the nitrogenous base contributes little or no surfactant character to these materials. In other words, the acids are generally capable of acting as surfactants when they are present as anions of the acid and the associated counterion is any positively charged species. The most common positively charged species are sodium, potassium, ammonium, calcium and magnesium ions. In fact, the acid portion of the polymerizable surfactant may be supplied as a sodium, potassium, or other salt of the carboxylic, phosphoric or sulfonic acid and then combined with the nitrogenous base to form the inventive surfactant.

The acids useful in the present invention are generally sulfonic acids, polysulfonic acids, sulfonic acids of oils, paraffin sulfonic acids, lignin sulfonic acids, petroleum sulfonic acids, tall oil acids, olefin sulfonic acids, hydroxyolefin sulfonic acids, polyolefin sulfonic acids, polyhydroxy polyolefin sulfonic acids, carboxylic acids, perfluorinated carboxylic acids, carboxylic acid sulfonates, alkoxylated carboxylic acid sulfonic acids, polycarboxylic acids, polycarboxylic acid polysulfonic acids, alkoxylated polycarboxylic acid polysulfonic acids, phosphoric acids, alkoxylated phosphoric acids, polyphosphoric acids, and alkoxylated polyphosphoric acids, fluorinated phosphoric acids, phosphoric acid esters of oils, phosphinic acids, alkylphosphinic acids, aminophosphinic acids, polyphosphinic acids, vinyl phosphinic acids, phosphonic acids, polyphosphonic acids, phosphonic acid alkyl esters, α-phosphono fatty acids, oragnoamine polymethylphosphonic acids, organoamino dialkylene phosphonic acids, alkanolamine phosphonic acids, trialkyledine phosphonic acids, acylamidomethane phosphonic acids, alkyliminodimethylene diphosphonic acids, polymethylene-bis(nitrilo dimethylene)tetraphosphonic acids, alkyl bis(phosphonoalkylidene) amine oxide acids, esters of substituted aminomethylphosphonic acids, phosphonamidic acids, acylated amino acids (e.g., amino acids reacted with alkyl acyl chlorides, alkyl esters or carboxylic acids to produce N-acylamino acids), N-alkyl acylamino acids, and acylated protein hydrolysates, and mixtures thereof.

Other acids which are useful in the present invention are selected from the group comprising linear or branched alkylbenzene sulfonic acids, alkyl sulfuric acid esters, alkoxylated alkyl sulfuric acid esters, α-sulfonated alkyl ester acids, α-sulfonated ester diacids, alkoxylated α-sulfonated alkyl ester acids, α-sulfonated dialkyl diester acids, di-α-sulfonated dialkyl diester acids, α-sulfonated alkyl acetate acids, primary and secondary alkyl sulfonic acids, perfluorinated alkyl sulfonic acids, sulfosuccinic mono- and diester acids, polysulfosuccinic polyester acids, sulfoitaconic diester acids, sulfosuccinamic acids, sulfosuccinic amide acids, sulfosuccinic imide acids, phthalic acids, sulfophthalic acids, sulfoisophthalic acids, phthalamic acids, sulfophthalamic acids, alkyl ketone sulfonic acids, bydroxyalkane-1-sulfonic acids, lactone sulfonic acids, sulfonic acid amides, sulfonic acid diamides, alkyl phenol sulfuric acid esters, alkoxylated alkyl phenol sulfuric acid esters, alkylated cycloalkyl sulfuric acid esters, alkoxylated alkylated cycloalkyl sulfuric acid esters, dendritic polysulfonic acids, dendritic polycarboxylic acids, dendritic polyphosphoric acids, sarcosinic acids, isethionic acids, and tauric acids, and mixtures thereof.

Additionally in accordance with the present invention, suitable acids of the present invention include fluorinated carboxylic acids, fluorinated sulfonic acids, fluorinated sulfate acids, fluorinated phosphonic and phosphinic acids, and mixtures thereof.

Due to their inherent hydrolytic instability, the sulfuric acid esters are preferably immediately converted to ethylenically unsaturated amine salts. For example, linear dodecyl alcohol is sulfated with $SO_3$ to produce an intermediate, hydrolytically unstable, dodecyl alcohol sulfate acid as shown in Scheme I below. The intermediate acid is neutralized with an ethylenically unsaturated nitrogenous base, such as allyl amine, to produce a dodecyl sulfate ethylenically unsaturated amine salt.

Scheme I: Formation of Dodecyl Sulfate Ethylenically Unsaturated Amine Salt

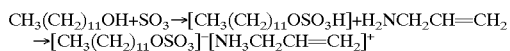

Additionally, for example, methyl laurate is sulfonated with $SO_3$ to produce an intermediate α-sulfonated lauryl methyl ester acid, as shown in Scheme II below. This acid is neutralized with an ethylenically unsaturated nitrogenous base, such as allyl amine, to produce an α-sulfonated lauryl methyl ester ethylenically unsaturated amine salt. Additionally, an α-sulfonated lauryl methyl ester ethylenically unsaturated amine di-salt may be produced as shown below in Scheme III. The α-sulfonated lauryl methyl ester ethylenically unsaturated amine salt and the α-sulfonated lauryl fatty acid ethylenically unsaturated amine di-salt may be formed as a mixture depending on the sulfonation conditions employed. The ratio of unsaturated amine salt to unsaturated amine di-salt is readily controlled by sulfonation conditions, well known to those skilled in the art.

Scheme II:
Formation of α-Sulfonated Lauryl Methyl Ester Ethylenically Unsaturated Amine

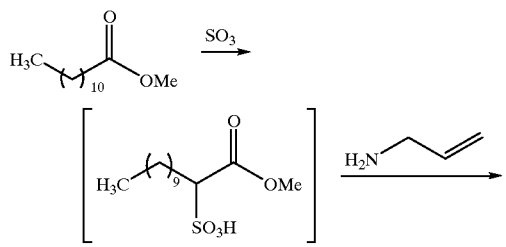

Scheme III:
Formation of α-Sulfonated Lauryl Methyl Ester Ethylenically Unsaturated Amine Di-Salt

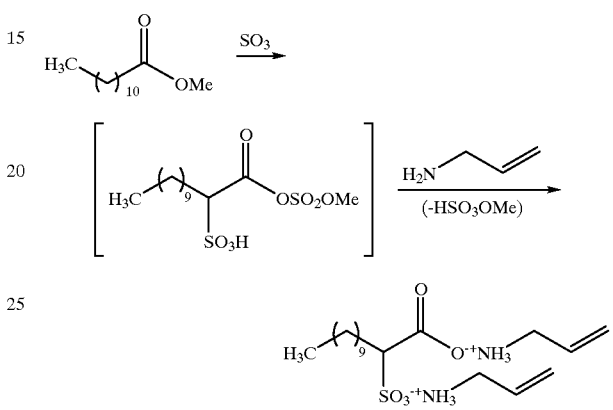

Ethylenically unsaturated amine salts of sulfosucinnate ester acids are typically produced by sulfitation of a succinic acid alkyl diester with sodium bisulfite, followed by ionic exchange with an ethylenically unsaturated nitrogenous base, such as allyl amine, as shown in Scheme IV below.

Scheme IV:
Formation of Sulfosuccinate Ester Ethylenically Unsaturated Amine Salt

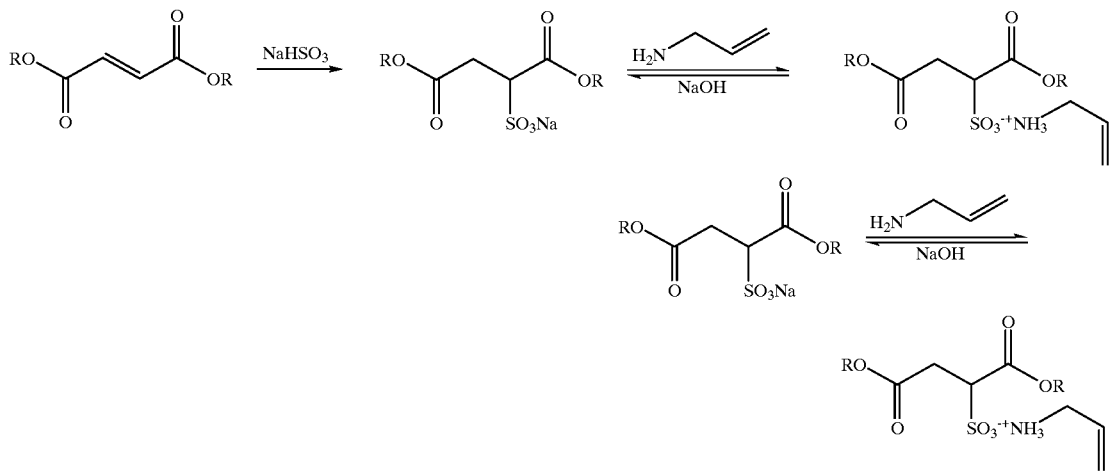

The sarcosinic acid ethylenically unsaturated amine salts are prepared by the amidation of a fatty acid, a fatty acid alkyl ester or a fatty acid chloride with sarcosine, followed by addition of an ethylenically unsaturated nitrogenous base, such as allyl amine, as shown in Scheme V below. Optionally, and somewhat less preferably, the ethylenically unsaturated nitrogenous base is combined with sarcosine to produce the corresponding sarcosine salt, which is then be used to amidate the fatty acid, fatty acid alkyl ester or fatty acid chloride.

Scheme V:
Formation Of A Fatty Sarcosinate Acid
Ethylenically Unsaturated Amine Salt

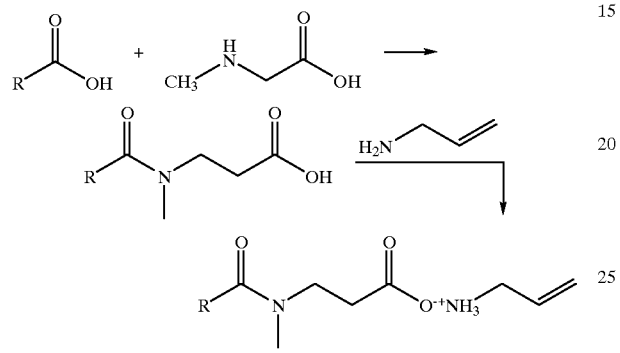

The isethionic acid ethylenically unsaturated amine salts may be prepared by the esterification of a fatty acid, a fatty acid alkyl ester or a fatty acid chloride with isethionic acid, followed by addition of an ethylenically unsaturated nitrogenous base, such as allyl amine, as shown in Scheme VI below. Additionally, isethionic acid ethylenically unsaturated amine salts may be prepared by esterifying a fatty acid, a fatty acid alkyl ester or a fatty acid chloride with the sodium salt of isethionic, followed by ion exchange with the ethylenically unsaturated nitrogenous base, such as allyl amine. Optionally, isethionic acid, or its sodium salt, may be combined with the ethylenically unsaturated nitrogenous base, such as allyl amine, to produce the isethionic acid allyl amine salt, which may then be esterified with a fatty acid, a fatty acid alkyl ester or a fatty acid chloride.

Scheme VI:
Formation Of A Isetionic Acid Ethylenically
Unsaturated Amine Salt

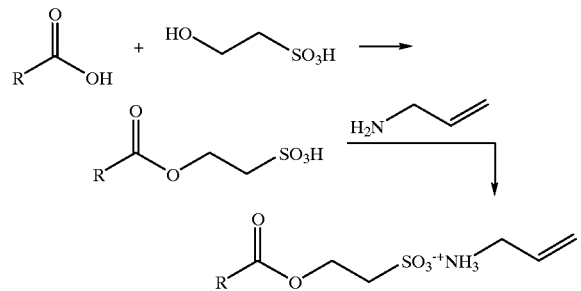

The preferred acids of the present invention are branched or linear alkylbenzene sulfonic acids, alkyl sulfuric acid esters, alkoxylated alkyl sulfuric acid esters, α-sulfonated alkyl ester acids, fatty carboxylic acids and phosphoric acid esters, and mixtures thereof. The most preferred acids of the present invention are branched or linear alkylbenzene sulfonic acids, alkyl sulfuric acid esters, and alkoxylated alkyl sulfuric acid esters, and mixtures thereof.

Another object of the present invention are sulfonic acid salts of ethylenically unsaturated amines, derived from sultone precursors, such as cyclic alkyl sultones. Examples of these sultone-derived sulfonic acid salts (e.g., allyl amine salts) include 2-acetamidoalkyl-1-sulfonates and amino carboxy acid alkyl sulfonates, as shown in Scheme VII and Scheme VIII below.

Scheme VII:
2-Acetamidoalkyl-1-Sulfonic
Acid Allyl Amine Salts

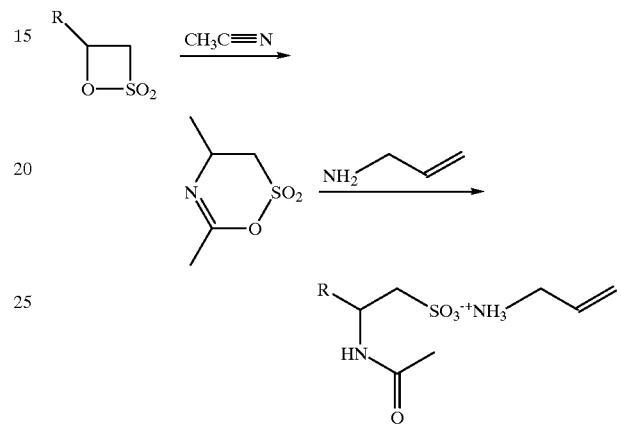

Scheme VIII:
Amino Carboxy Acid Alkyl Sulfonic Acid Allyl Amine Salts

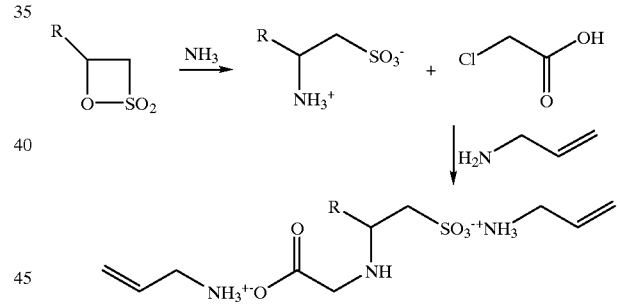

In general, nitrogenous bases, which are useful in the present invention are any nitrogenous base which contains an ethylenically unsaturated moiety, including various vinyl amines. In addition to allyl amine, as shown in the above schemes, other examples of nitrogenous bases that are useful in the present invention are ethylenically unsaturated amines selected from the group comprising vinyl amine, N-methyl N-allyl amine, $C_1$–$C_{24}$ alkyl allyl amine, $C_1$–$C_{24}$ alkyl ethoxylated and/or propoxylated allyl amine, $C_1$–$C_{24}$ dialkyl allyl amine, ethoxylated and/or propoxylated allyl amine diallyl amine, $C_1$–$C_{24}$ alkyl diallyl amine, ethoxylated and/or propoxylated diallyl amine, triallyl amine, 1,2-diaminoethene, aminocrotonitrile, diaminomaleonitrile, N-allylcyclopentylamine, N-allylaniline, allylcyclohexylamine, [1-(2-allylphenoxy)-3-(isopropylamino)-2-propanol], 3-amino-2-butenethioamide, bis[4-(dimethylamino)-benzylidene]acetone, 1,4-butanediol bis(3-aminocrotonate), 3-amino-1-propanol vinyl ether, 2-(diethylamino)ethanol vinyl ether, 4-(diethylamino) cinnamaldehyde, 4-(diethylamino)cinnamonitrile, 2-(diethylamino)ethyl methacrylate, diethyl (6-methyl-2-pyridylaminomethylene)maleate, 3-(dimethylamino) acrolein, 2-(dimethylamino)ethyl methacrylate, 4-dimethylaminocinnamaldehyde, 2-(dimethylamino)ethyl acrylate, 3-(dimethylamino)-2-methyl-2-propenal, 9-vinylcarbazole, N-vinylcaprolactam, 1-vinylimidazole, 2-vinylpyridine, 4-vinylpyridine, allylcyclohexylamine, N-allylcyclopentylamine, allyl(diisopropylamino) dimethylsilane, 1-allylimidazole, 1-vinyl-2-pyrrolidinone, N-[3-(dimethylamino)propyl]methacrylamide, 4-[4-(dimethylamino)styryl]pyridine, 2-[4-(dimethylamino) styryl]pyridine, 2-[4-(1,2-diphenyl-1-butenyl)phenoxy]-N,N-dimethylethylamine, 2-[4-dimethylamino)styryl]-benzothiozole, 5-[4-(dimethylamino)phenyl]-2,4pentandienal, (dimethylamino-methylene)malononitrile, 4-dimethylaminocirnamonitrile, 4-(dimethylamino) chalcone, [6-(3,3-dimethylallylamino-purine riboside, 3,7-dimethyl-2,6-octadien-1-ylamine, 2-isopropenylaniline, isopropyl 3-aminocrotonate, S-{2-[3-(hexyloxy)benzoyl]-vinyl}glutathione, methyl 3-aminocrotonate, N-methylallylamine, N-methyl-1-(methylthio)-2-nitroetheneamine, oleylamine, tetrakis(dimethylamino) ethylene, 5-[(6,7,8-trimethoxy4-quinazolinyl)amino]-1-pentanol nitrate ester, tris(2-methylallyl)amine, N,N,N',N'-tetramethyl-2-butene-1,4-diamine, S-{2-[3-(octyloxy) benzoyl]vinyl}-glutathione, 4,4'-vinylidene-(N,N-dimethylaniline), 2',5'-dimethoxy-4-stilbenamine, 3-(dimethylamino)propyl acrylate, 3-dimethylaminoacrylonitrile, 4-(dimethylamino)-cinnamic acid, 2-amino-1-propene-1,1,3-tricarbonitrile, 2-amino-4-pentenoic acid, N, N'-diethyl-2-butene-1,4-diamine, 10,11-dihyro-N,N-dimethyl-5-methylene-5H-dibenzo[a,d]-cyclohepene-10-ethanamine maleate, 4-(dicyanomethylene)-2-methyl-6-(4-dimethyl-aminostyryl)-4H-pyran, N-ethyl-2-methylallylamine, ethyl 3-aminocrotonate, ethyl-α-cyano-3-indoleacrylate, ethyl-3-amino-4,4-dicyano-3-butenoate, 1,3-divinyl-1,1,3,3-tetramethyldisilazane, N-(4,5-dihydro-5-oxo-1-phenyl-1H-pyrazol-3-yl)-9-octadecen-amide, and N-oleoyl-tryptophan ethyl ester, and mixtures thereof.

More preferred nitrogenous bases of the present invention are allyl amine, diallyl amine, triallyl amine, methylallyl amine, allyldimethyl amine, methyl 3-amino crotonate, 3-amino crotononitrile, 3-amino-1-propanol vinyl ether, N-methyl N-allyl amine, 2-(dimethylamino)ethyl acrylate, or 1,4-diamino-2-butene, and mixtures thereof. The most preferred nitrogenous bases of the present invention are allyl amine, diallyl amine, triallyl amine, methallyl amine, N-methyl N-allyl amine, and 2-(dimethylamino)ethyl acrylate, and mixtures thereof.

Accordingly, the present invention encompasses surface active agents of the formula:

$(R_1)_n$—$Ar(SO_3^-M^+)_m$ 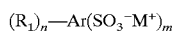

wherein $R_1$ is a saturated or unsaturated hydrocarbon group having from about 1–24 carbon atoms; wherein Ar is a phenyl, polyphenyl, napthyl, polynapthyl, styryl, or polystyryl group, or a mixture thereof; wherein $M^+$ is a conjugate acid of the nitrogenous base; wherein n=1–5 and m=1–8; and wherein the total number of carbon atoms represented by $(R_1)_n$ is at least 5. In a preferred embodiment $R_1$ is a saturated or unsaturated hydrocarbon group having from about 6–24 carbon atoms, Ar is a phenyl, $M^+$ is a conjugate acid of the nitrogenous base, the nitrogenous base selected from the group consisting of allyl amine, diallyl amine, triallyl amine, methallyl amine, N-methyl N-allyl amine or 2-(dimethylamino)ethyl acrylate, and mixtures thereof and n=1 and m=1. In another preferred embodiment, the surface active agent is of the formula:

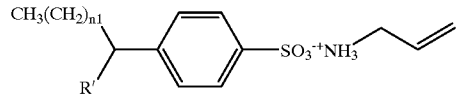

wherein n1=4–18; and wherein R' is hydrogen or saturated or unsaturated hydrocarbon group having from about 1–8 carbon atoms.

The present invention further encompasses surface active agents of the formula $(R_1)_{n1}$—{$Ar(SO_3^-M^+)_{m1}$}—O—{$Ar(SO_3^-M^+)_{m2}$}—$(R_2)_{n2}$ 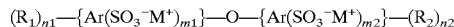

wherein $R_1$ and $R_2$ are independently hydrogen, or saturated or unsaturated hydrocarbon groups having from about 1–24 carbon atoms; wherein Ar is a phenyl, polyphenyl, napthyl, polynapthyl, styryl, or polystyryl group, or a mixture thereof; wherein $M^+$ is a conjugate acid of the nitrogenous base; wherein n1 and n2 are independently 0–5, provided that n1 and n2 are not both equal to zero; and wherein m1 and m2 are independently 0–8, provided that m1 and m2 are not both equal to zero. In a preferred embodiment, $R_1$ is hydrogen and $R_2$ is a saturated or unsaturated hydrocarbon group having from about 6–24 carbon atoms, Ar is phenyl, $M^+$ is a conjugate acid of the nitrogenous base, the nitrogenous base selected from the group consisting of allyl amine, diallyl amine, triallyl amine, methallyl amine, N-methyl N-allyl amine or 2-(dimethylamino)ethyl acrylate, and mixtures thereof, n1=4, n2=1, and m1 and m2 both equal one. In another preferred embodiment, $R_1$ and $R_2$ are independently saturated or unsaturated hydrocarbon groups having from about 6–24 carbon atoms, Ar is phenyl, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, n1 and n2 both equal one, and m1 and m2 both equal one. In another preferred embodiment, the surface active agent is of the formula:

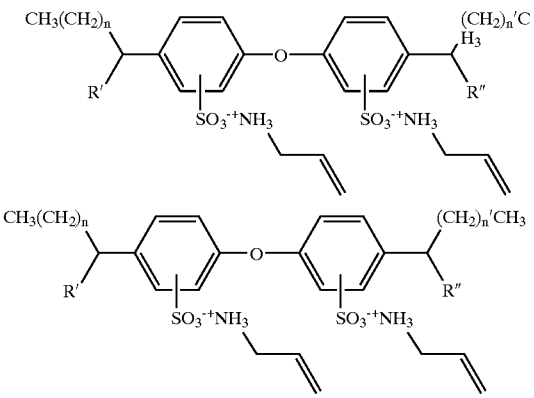

wherein n and n' are independently 4–18; and wherein R' and R" are independently hydrogen, methyl, ethyl or propyl.

The present invention further encompasses surface active agents of the formula:

$R_1$—$CH(SO_3^-M^+)CO_2R_2$ 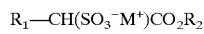

wherein $R_1$ and $R_2$ are independently saturated or unsaturated hydrocarbon groups having from about 1–24 carbon atoms; and wherein M⁺ is a conjugate acid of the nitrogenous base. In a preferred embodiment, R₁ is a saturated or unsaturated hydrocarbon group having from about 6–24 carbon atoms, R₂ is methyl, ethyl, or propyl, or a mixture thereof, and M⁺ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

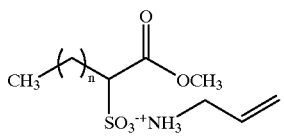

wherein n=3–18.

The present invention further encompasses surface active agents of the formula:

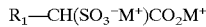

wherein R₁ is a saturated or unsaturated hydrocarbon group having from about 3–24 carbon atoms; and wherein M⁺ is a conjugate acid of the nitrogenous base. In a preferred embodiment, R₁ is a saturated or unsaturated hydrocarbon group having from about 6–24 carbon atoms, M⁺ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

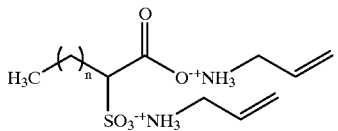

wherein n=3–18.

The present invention further encompasses surface active agents of the formula:

wherein R₁ and R₂ are independently saturated or unsaturated hydrocarbon groups having from about 1–24 carbon atoms; wherein R' is methyl or hydrogen; wherein n=1–100; and wherein M⁺ is a conjugate acid of the nitrogenous base. In a preferred embodiment, R₁ is a saturated or unsaturated hydrocarbon group having from about 4–24 carbon atoms, R' is methyl or hydrogen, R₂ is methyl, ethyl, or propyl, and mixtures thereof, M⁺ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, and n=1–100. In another preferred embodiment, the surface active agent is of the formula:

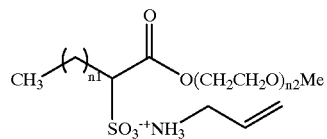

wherein n1=2–18; and wherein n2=1–20.

The present invention further encompasses surface active agents of the formula:

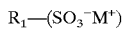

wherein R₁ is a saturated or unsaturated hydrocarbon group having from about 6–24 carbon atoms and wherein M⁺ is a conjugate acid of the nitrogenous base. In a preferred embodiment, R₁ is a saturated or unsaturated hydrocarbon group having from about 6–24 carbon atoms, and M⁺ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

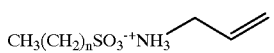

wherein n=5–17.

The present invention further encompasses surface active agents of the formula:

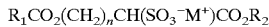

wherein R₁ and R₂ are independently saturated or unsaturated hydrocarbon groups having from about 1- 24 carbon atoms; wherein n=0–10; and wherein M⁺ is a conjugate acid of the nitrogenous base. In a preferred embodiment, R₁ and R₂ are independently saturated or unsaturated hydrocarbon groups having from about 1–24 carbon atoms, n=1–6, and M⁺ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

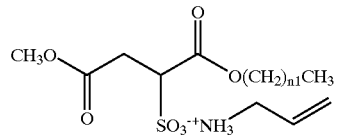

wherein n1=0–17

The present invention further encompasses surface active agents of the formula:

wherein R₁ is a saturated or unsaturated hydrocarbon group having from about 1–24 carbon atoms; wherein n=1–10; and wherein M⁺ is a conjugate acid of the nitrogenous base. In a preferred embodiment, R₁ is a saturated or unsaturated hydrocarbon group having from about 6–24 carbon atoms, n=1–5, and M⁺ is a conjugate acid of the nitrogenous base, the nitrogenous base selected from the group consisting essentially of allyl amine, diallyl amine, triallyl amine, methallyl amine, N-methyl N-allyl amine, or 2-(dimethylamino)ethyl acrylate, or a mixture thereof. In another preferred embodiment, the surface active agent is of the formula:

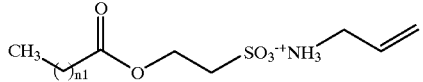

wherein n1=2–18.

The present invention further encompasses surface active agents of the formula:

$(R_1)_n$—Ar—O(CH$_2$CH(R')O)$_m$(SO$_3^-$M$^+$)

wherein $R_1$ is a saturated or unsaturated hydrocarbon group having from about 1–24 carbon atoms; wherein Ar is a phenyl, polyphenyl, napthyl, polynapthyl, styryl, or polystyryl group, and mixtures thereof; wherein R' is methyl or hydrogen; wherein M$^+$ is a conjugate acid of the nitrogenous base; wherein n=1–4; wherein the total number of carbon atoms represented by $(R_1)_n$ is at least 5; and wherein m=0–100. In a preferred embodiment, $R_1$ is a saturated or unsaturated hydrocarbon group having from about 6–24 carbon atoms, Ar is phenyl; M$^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, n=1, and m=0–100. In another preferred embodiment, the surface active agent is of the formula:

wherein n1=5–18; and wherein n2=0–20.

The present invention further encompasses surface active agents of the formula:

$R_1O(CH_2CH(R')O)_n(SO_3^-M^+)$ wherein $R_1$ is a saturated or unsaturated hydrocarbon group having from about 1–24 carbon atoms; wherein R' is methyl or hydrogen; wherein n=0–100; and wherein M$^+$ is a conjugate acid of the nitrogenous base. In a preferred embodiment, $R_1$ is a saturated or unsaturated hydrocarbon group having from about 6–24 carbon atoms, R' is methyl or hydrogen, n=0–100, and M$^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

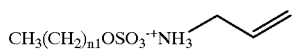

wherein n1=5–18. In another preferred embodiment, the surface active agent is of the formula:

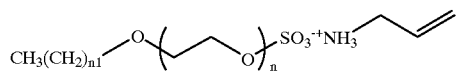

wherein n1=5–18; and wherein n=1–20.

The present invention further encompasses surface active agents of the formula:

$R_1CO_2^-M^+$ wherein $R_1$ is a saturated or unsaturated hydrocarbon group having from about 4–24 carbon atoms; and wherein M$^+$ is a conjugate acid of the nitrogenous base. In a preferred embodiment, $R_1$ is a saturated or unsaturated hydrocarbon group having from about 6–24 carbon atoms, and M$^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof. In another preferred embodiment, the surface active agent is of the formula:

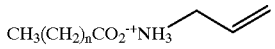

wherein n=5–18.

The present invention further encompasses surface active agents of the formula:

$R_1CON(R')(CH_2)_nCO_2^-M^+$ wherein $R_1$ is a saturated or unsaturated hydrocarbon group having from about 1–24 carbon atoms; wherein R' is methyl, ethyl, propyl or hydrogen; wherein M$^+$ is a conjugate acid of the nitrogenous base; and wherein n=1–10. In a preferred embodiment, M$^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, R' is methyl, ethyl, propyl or hydrogen, and n=2–5. In another preferred embodiment, the surface active agent is of the formula:

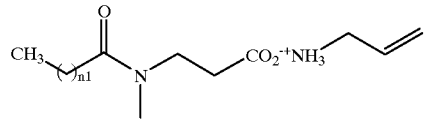

wherein n1=2–18.

The present invention further encompasses surface active agents of the formula:

$R_1CON(R')(CH_2)_nSO_3^-M^+$ wherein $R_1$ is a saturated or unsaturated hydrocarbon group having from about 1–24 carbon atoms; wherein R' is methyl, ethyl, propyl or hydrogen; wherein M$^+$ is a conjugate acid of the nitrogenous base; and wherein n=1–10. In a preferred embodiment, M$^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof, R' is methyl, ethyl, propyl or hydrogen, and n=2–5. In another preferred embodiment, the surface active agent is of the formula:

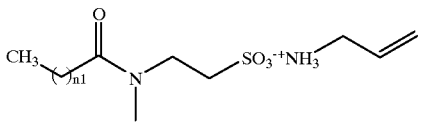

wherein n1=2–18.

The present invention further encompasses surface active agents of the formula:

$$R_1O(CH_2CH(R')O)_nCOCH_2SO_3^-M^+$$

wherein $R_1$ is a saturated or unsaturated hydrocarbon group having from about 1–24 carbon atoms; wherein R' is methyl or hydrogen; wherein n=0–100; wherein $M^+$ is a conjugate acid of the nitrogenous base. In a preferred embodiment, $R_1$ is a saturated or unsaturated hydrocarbon group having from about 6–24 carbon atoms; R' is methyl or hydrogen, $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof; and n=0–100. In another preferred embodiment, the surface active agent is of the formula:

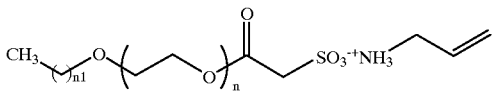

wherein n1=5–17; and wherein n=0–20.

The present invention further encompasses surface active agents of the formula:

$$R_1O(PO_3)_x^-M^+_y$$

wherein $R_1$ is a saturated or unsaturated hydrocarbon group having from about 1–24 carbon atoms, phenyl, polyphenyl, napthyl, polynapthyl, styryl, or polystyryl group, an alkyl/alkoxylate substituted phenyl, an alkyl/alkoxylate substituted or poly-substituted polyphenyl, an alkyl/alkoxylate substituted or poly-substituted napthyl, an alkyl/alkoxylate substituted or poly-substituted polynapthyl, an alkyl/alkoxylate substituted or poly-substituted styryl, or an alkyl/alkoxylate substituted or poly-substituted polystyryl group, and mixtures thereof; wherein $M^+$ is a conjugate acid of the nitrogenous base; wherein x=1 or 2; and wherein y=1 or 2.

The present invention further encompasses surface active agents of the formula:

$$[R_1O(CH_2CH(R')O)_m]_nP(O)_p^{x-}M^+_y$$

wherein $R_1$ is a saturated or unsaturated hydrocarbon group having from about 1–24 carbon atoms; wherein R' is methyl or hydrogen; wherein $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof; m=0–100; wherein n=1 or 2; wherein p=2 or 3; wherein x=1 or 2; and wherein y=1 or 2.

The present invention further encompasses surface active agents of the formula:

$$[(R_1)_nArO(CH_2CH(R')O)_m]_qP(O)_p^{x-}M^+_y$$

wherein $R_1$ is a saturated or unsaturated hydrocarbon group having from about 1–24 carbon atoms; wherein Ar is phenyl; wherein R' is methyl or hydrogen; wherein $M^+$ is a conjugate acid of the nitrogenous base, the nitrogenous base selected from the group consisting of allyl amine, diallyl amine, triallyl amine, methallyl amine, N-methyl N-allyl amine, or 2-(dimethylamino)ethyl acrylate, and mixtures thereof; wherein n=1–4; wherein m=0–100; wherein q=1 or 2; wherein p=2 or 3; wherein x=1 or 2; and wherein y=1 or 2.

The present invention further encompasses polymerizable surface active agents which are quaternary ammounium salts of the general formula:

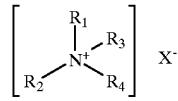

wherein $R_1$, $R_2$, $R_3$, and $R_4$ are independently, substituted or unsubstituted hydrocarbyl groups of from about 1 to about 30 carbon atoms, or hydrocarbyl groups having from about 1 to about 30 carbon atoms and containing one or more aromatic, ether, ester, amido, or amino moieties present as substituents or as linkages in the radical chain, wherein at least one of the $R_1$-$R_4$ groups contains at least one or more ethenylene groups; and wherein $X^-$ is an anion group selected from the group consisting of sulfonate, sulfate, sulfmate, sulfenate, phosphate, carboxylate, nitrate, and acetate. Polymerizable surface active agents of the present invention include those of the above general formula in the form of ring structures formed by covalently linking two of the $R_1$-$R_4$ groups. Examples include unsaturated imidazolines, imidazoliniums, and pyridiniums, and the like.

The disclosures of all documents, e.g., patents and journal articles, cited above or below are hereby incorporated by reference in their entirety.

In the following examples, all amounts are stated in percent by weight of active material unless indicated otherwise. One skilled in the art will recognize that modifications may be made in the present invention without deviating from the spirit or scope of the invention. The invention is illustrated further by the following examples which are not to be construed as limiting the invention or scope of the specific procedures or compositions described herein. As used in the examples appearing below, the following designations, symbols, terms and abbreviations have the indicated meanings:

| Material | Definition |
| --- | --- |
| Polystep ® A-13 | Linear dedecylbenzene sulfonic acid (commercially avaiable from Stepan Company, Northfield Illinois) |
| Polystep ® A-16 | Branched dodecylbenzene sulfonic acid, sodium salt (commercially available from Stepan Company, Northfield Illinois) |
| Polystep ® A-17 | Branched dodecylbenzene sulfonic acid (commercially avaiable from Stepan Company, Northfield Illinois) |
| Cedephos CP-610 | Nonyl Phenol 9-EO Phosphoric Acid Ester (commercially available from Stepan Company, Northfield Illinois) |

Procedures

Due to their amphiphilic character, surfactants have a tendency to adsorb at various liquid-liquid interfaces, which leads to a reduction of surface or interfacial tension. After saturating an interface, these surface active molecules begin to aggregate in the solution to form micelles at a specific surfactant concentration known as the critical micelle concentration (CMC). The adsorption characteristics and the micellization behavior of surfactants are responsible for the technologically important properties of surfactants, such as foaming, detergency, wetting, solubilization, emulsification, and the like. Thus, the efficiency of any surface active agent relates to its ability to lower interfacial tension, form micelles, and display favorable adsorption characteristics by providing efficient packing of the surface active molecules at the interface in a very small concentration.

The following test procedures were used to evaluate the ethylenically unsaturated amine salts of the present invention. A fully automated Kruss K-12 tensiometer was used to measure the adsorption and micellar behavior of the polymerizable, surface active agents. All of the measurements were done at room temperature, and distilled water was used for CMC measurements. Interfacial tension between a 0.3% active surfactant solutions and mineral oil was measured using a spinning drop tensiometer as developed by the University of Texas.

All $^1$H NMR spectra were recorded using a 270 MHz Joel Delta NMR Fourier Transform Spectrometer. Chemical shifts ($\delta$) are reported in parts per million (ppm) down field from tetramethylsilane (TMS) using internal TMS or residual non-deuterated solvent as a reference. Multiplicity is indicated by the following abbreviations: singlet (s), doublet (d), triplet (t), quartet (q), heptet (h), multiplet (m), broad multiplet (br m) doublet of doublets (dd), etc. All samples were isolated in solid form by oven-drying aqueous solution of the surface active agents to remove substantially all water from the sample; NMR data for all samples was acquired by dissolving the solid sample in $CD_3OD$.

EXAMPLE #1

Approximately 7.5 ml of allyl amine and about 150.0 g of deionized water were charged to a reaction vessel equipped with a means for agitation and a means for cooling. The allyl amine/water mixture temperature was adjusted to about 25° C. and approximately 32.5 g of Polystep® A-13 was added, to give the desired ethylenically unsaturated amine salt as an approximately 20% active aqueous solution with a pH of about 6.5. The pH of the resulting salt solution may be adjusted as needed with the addition of more acid or amine; higher and lower pH materials may be produced as desired. $^1$H NMR: $\delta$ 7.8 (m, 2H), 7.2 (m, 2H), 6.0 (m, 1H), 5.4 (ddt, 2H), 5.0 (br, 3H), 3.6 (m, 2H), 1.7 (bm, 3H), 1.3 (bm, 16H), 0.9 (m, 6H). The CMC, Surface Tension Reduction, and Effectiveness of Surfactant are reported in Table I.

EXAMPLE #2

Approximately 7.5 ml of allyl amine and about 150.0 g of deionized water were charged to a reaction vessel equipped with a means for agitation and a means for cooling. The allyl amine/water mixture temperature was adjusted to about 25° C. and approximately 32.5 g of Polystep® A-17 was added, to give the desired ethylenically unsaturated amine salt as an approximately 20% active aqueous solution with a pH of about 7.0. The pH of the resulting salt solution may be adjusted as needed with the addition of more acid or amine; higher and lower pH materials may be produced as desired. $^1$H NMR: $\delta$ 7.8 (m, 2H), 7.4 (bt, 2H), 5.9 (ddt, 1H), 5.4 (m, 2H), 4.9 (br, 3H), 3.5 (dd, 2H), 2.9 (m, 1H), 1.6 (m, 3H), 0.9–1.1 (m, 28H).

EXAMPLE #3

Approximately 12.3 ml of diallyl amine and about 170.0 g of deionized water were charged to a reaction vessel equipped with a means for agitation and a means for cooling. The diallyl amine/water mixture temperature was adjusted to about 25° C. and approximately 32.5 g of Polystep® A-13 was added, to give the desired ethylenically unsaturated amine salt as an approximately 20% active aqueous solution with a pH of about 7.0. The pH of the resulting salt solution may be adjusted as needed with the addition of more acid or amine; higher and lower pH materials may be produced as desired. $^1$H NMR: $\delta$ 7.8 (m, 2H), 7.2 (m, 2H), 6.0 (m, 2H), 5.4 (m, 4H), 5.0 (br, 2H), 3.6 (m, 4H), 1.7 (bm, 4H), 1.3 (bm, 15H), 0.9 (bm, 6H).

EXAMPLE #4

Approximately 12.3 ml of diallyl amine and about 170.0 g of deionized water were charged to a reaction vessel equipped with a means for agitation and a means for cooling. The allyl amine/water mixture temperature was adjusted to about 25° C. and approximately 32.5 g of Polystep® A-17 was added, to give the desired ethylenically unsaturated amine salt as an approximately 20% active aqueous solution with a pH of about 7.0. The pH of the resulting salt solution may be adjusted as needed with the addition of more acid or amine; higher and lower pH materials may be produced as desired. $^1$H NMR: $\delta$ 7.8 (m, 2H), 7.5 (m, 2H), 5.9 (m, 2H), 5.4 (m, 4H), 4.9 (brs, 2H), 3.6 (m, 4H), 2.8 (m, 1H), 1.7 (bm, 3H), 0.9–1.1 (m, 28H).

EXAMPLE #5 (COMPARATIVE EXAMPLE)

Approximately 13.7 ml of propyl amine and about 170.0 g of deionized water were charged to a reaction vessel equipped with a means for agitation and a means for cooling. The propyl amine/water mixture temperature was adjusted to about 25° C. and approximately 32.5 g of Polystep® A-13 was added, to give the saturated amine salt as an approximately 20% active aqueous solution with a pH of about 7.0. The pH of the resulting salt solution may be adjusted as needed with the addition of more acid or amine; higher and lower pH materials may be produced as desired. $^1$H NMR: $\delta$ 7.8 (dd, 2H0, 7.23 (t, 2H), 4.9 (br, 2H), 2.85 (t, 2H), 1.6 (m, 6H), 1.2 (m, 14H), 0.9 (m, 6H). The CMC, Surface Tension Reduction, and Effectiveness of the Surfactant are reported in Table I.

EXAMPLE #6

Approximately 30.0 ml of allyl amine and about 408.0 g of deionized water were charged to a reaction vessel equipped with a means for agitation and a means for cooling. The allyl amine/water mixture temperature was adjusted to about 25° C. and approximately 80.0 g of lauric acid was added, to give the desired ethylenically unsaturated amine salt as an approximately 20% active aqueous solution with a pH of about 7.0. (The carboxylic acid may be a solid at room temperature and can be pre-melted prior to addition to the amine/water mixture, for ease of handling. As an alternative, the carboxylic acid and water may be combined and heated to produce a uniform mixture, i.e., 50–60° C. for lauric acid, followed by addition of the unsaturated amine.) The pH of the resulting salt solution may be adjusted as needed with the addition of more acid or amine; higher and lower pH materials may be produced as desired. $^1$H NMR: $\delta$ 6.0 (m, 1H), 5.5 (ddt, 2H), 3.6 (m, 2H), 2.3 (t, 2H), 1.6 (br, 2H), 1.42 (s, 5H, residual water), 1.41 (s, 3H), 1.4 (br, 18H), 0.9 (t, 3H).

EXAMPLE #7 (COMPARATIVE EXAMPLE)

Approximately 16.4 ml of propyl amine and about 210.0 g of deionized water were charged to a reaction vessel equipped with a means for agitation and a means for cooling. The propyl amine/water mixture temperature was adjusted to about 25° C. and approximately 40.0 g of lauric acid was added, to give the saturated amine salt as an approximately 20% active aqueous solution with a pH of about 7.0. (The carboxylic acid may be a solid at room temperature and can be pre-melted prior to addition to the amine/water mixture, for ease of handling. As an alternative, the carboxylic acid and water may be combined and heated to produce a uniform mixture, i.e., 50–60° C. for lauric acid, followed by addition of the saturated amine.) The pH of the resulting salt solution may be adjusted as needed with the addition of more acid or amine; higher and lower pH materials may be produced as desired. $^1$H NMR: $\delta$ 5.0 (s, 3H), 3.3 (p, 2H), 2.8 (dt, 2H), 2.25 (t, 2H), 1.6 (m, 2H), 1.3 (m, 17H), 1.0 (t, 3H), 0.9 (t, 3H).

EXAMPLE #8

Approximately 5.1 ml of allyl amine and about 320.0 g of deionized water were charged to a reaction vessel equipped with a means for agitation and a means for cooling. The allyl amine/water mixture temperature was adjusted to about 25° C. and approximately 75.0 g of CP-610 was added, to give the desired unsaturated amine salt as an approximately 20% active aqueous solution with a pH of about 7.0. (The phosphoric acid ester may be a solid at room temperature and can be pre-melted prior to addition to the amine/water mixture, for ease of handling. As an alternative, the phosphoric acid ester and water may be combined and heated to produce a uniform mixture, followed by addition of the unsaturated amine.) The pH of the resulting salt solution may be adjusted as needed with the addition of more acid or amine; higher and lower pH materials may be produced as desired. $^1$H NMR: $\delta$ 7.2 (m, 2H), 6.8 (m, 2H), 6.0 (m, 1H), 5.4 (m, 2H), 4.1 (m, 2H), 3.8 (m, 2H), 3.6 (m, 32H), 0.4–1.8 (m, 19H). The CMC, Surface Tension Reduction, and Effectiveness of the Surfactant are reported in Table I.

EXAMPLE #9 (COMPARATIVE EXAMPLE)

Approximately 5.1 ml of propyl amine and about 320.0 g of deionized water were charged to a reaction vessel equipped with a means for agitation and a means for cooling. The allyl amine/water mixture temperature was adjusted to about 25° C. and approximately 75.0 g of CP-610 was added, to give the desired unsaturated amine salt as an approximately 20% active aqueous solution with a pH of about 7.0. (The phosphoric acid ester may be a solid at room temperature and can be pre-melted prior to addition to the amine/water mixture, for ease of handling. As an alternative, the phosphoric acid ester and water may be combined and heated to produce a uniform mixture, followed by addition of the unsaturated amine.) The pH of the resulting salt solution may be adjusted as needed with the addition of more acid or amine; higher and lower pH materials may be produced as desired. $^1$H NMR: $\delta$ 7.2 (m, 2H), 6.8 (m, 2H), 4.9 (s, 3H), 4.1 (m, 2H), 3.8 (m, 2H), 3.6 (m, 32H), 3.3 (t, 2H), 2.9 (dt, 2H), 0.4–1.8 (m, 22H). The CMC, Surface Tension Reduction, and Effectiveness of the Surfactant are reported in Table I.

TABLE I

Surface Tension Data for Ethylenically Unsaturated Amine Salts of Sulfonic Acids, Carboxylic Acids and Phosphoric Acid Esters, Including Comparative Examples

| Example # | Ethylenically Unsaturated Amine Salt | CMC (mg/l) | Surface Tension at CMC (mN/m) | Effectiveness of Surface Tension Reduction at CMC (mN/m) |
|---|---|---|---|---|
| 1 | Allylamine Salt of Dodecylbenzene Sulfonic Acid | 100.5 | 33.2 | 39.1 |
| 5 (comparative) | Propylamine Salt of Dodecylbenzene Sulfonic Acid | 480.5 | 31.0 | 41.3 |
| Polystep ® A-16 | Sodium Salt of Dodecylbenzene Sulfonic Acid | 156.0 | 35.0 | 37.3 |
| 8 | Allylamine Salt of Nonylphenol 9-EO Phosphoric Acid Ester | 31.8 | 30.0 | 42.3 |
| 9 (comparative) | Propylamine Salt of Nonylphenol 9-EO Phosphoric Acid Ester | 74 | 31.5 | 40.8 |

EXAMPLE #10

Emulsion Polymerization With Polystep A-17 Allyl Amine Salt

An emulsion polymerization kettle equipped with a nitrogen inlet, a heating means, and an agitation means, is charged with 250 g of water and 8.13 g of Polystep A-17 allyl amine salt. The mixture is heated to approximately 85° C. Approximately 17 g of a 4% aqueous ammonium persulfate solution (i.e. initiator solution) is added and approximately 75 g of monomer solution is added while mixing, the monomer solution comprising 48% butyl acrylate, 49% methyl methacrylate and 3% methacrylic acid. After mixing for 15 minutes, 298 g of monomer solution is added over 2.5 hours. After monomer solution addition is complete, 67 g of initiator solution and 75 g of Polystep A-17 allyl amine salt, in 35 g of water, are added separately and concurrently, over 2 hours. The resulting mixture is agitated at 85° C. for another hour followed by discharging the reactor to give an all acrylic latex with the following properties: Viscosity: 50 centipoise; pH: 6.4; Solids: 45.6(actual), 46.7(theoretical); Particle Size: 115.

From the foregoing, it will be appreciated that although specific embodiments of the invention have been described herein for purposes of illustration, various embodiments may be made without deviating from the spirit or scope of the invention.

What is claimed:

1. A polymerizable surface active agent comprising an amine salt comprising:
   a) a conjugate base derived from an acid of the formula $R_1$—CH(SO$_3$H)CO$_2$R$_2$, wherein $R_1$ is a saturated or unsaturated hydrocarbon group having from about 6–24 carbon atoms; $R_2$ is methyl, ethyl, or propyl, or a mixture thereof; and b) a conjugate acid derived from a nitrogenous base, wherein the nitrogenous base is selected from the group consisting of allyl amine, diallyl amine, triallyl amine, methallyl amine, N-methyl N-allyl amine, 2-(dimethylamino)ethyl acrylate, and mixtures thereof.

2. A polymerizable, surface active agent according to claim 1, which has the formula:

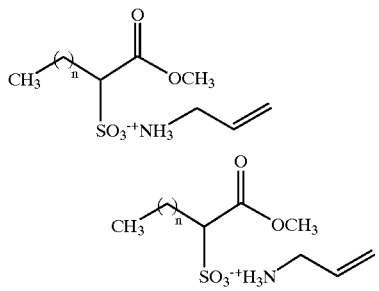

wherein n=3–18.

3. An aqueous, surface active solution comprising water and the polymerizable, surface active agent of claim 1.

4. A polymerizable, surface active agent comprising an amine salt comprising:

a) a conjugate base derived from an acid of the formula $R_1$—$CH(SO_3H)CO_2H$, wherein $R_1$ is a saturated or unsaturated hydrocarbon group having from about 6–24 carbon atoms; and b) a conjugate acid derived from a nitrogenous base, wherein the nitrogenous base is selected from the group consisting of allyl amine, diallyl amine, triallyl amine, methallyl amine, N-methyl N-allyl amine, 2-(dimethylamino)ethyl acrylate, and mixtures thereof.

5. A polymerizable, surface active agent according to claim 4, which has the formula:

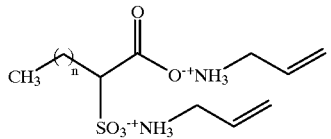

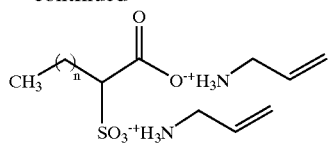

wherein n=3–18.

6. An aqueous, surface active solution comprising water and the polymerizable surface active agent of claim 4.

7. A polymerizable surface active agent comprising an amine salt comprising:

a) a conjugate base derived from an acid of the formula $R_1$—$(SO_3H)$, wherein $R_1$ is a saturated or unsaturated hydrocarbon group having from about 6–24 carbon atoms; and b) a conjugate acid derived from a nitrogenous base, wherein the nitrogenous base is selected from the group consisting of allyl amine, diallyl amine, triallyl amine, methallyl amine, N-methyl N-allyl amine, 2-(dimethylamino)ethyl acrylate, and mixtures thereof.

8. A polymerizable, surface active agent according to claim 7, which has the formula:

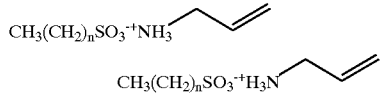

wherein n=5–17.

9. An aqueous, surface active solution comprising water and the polymerizable surface active agent of claim 7.

10. A polymerizable, surface active agent comprising an amine salt which has the formula:

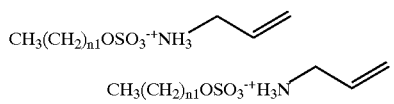

wherein n1=5–18.

* * * * *